United States Patent
Qi et al.

(10) Patent No.: US 6,933,291 B2
(45) Date of Patent: Aug. 23, 2005

(54) CHOLESTEROL LOWERING SUPPLEMENT

(75) Inventors: Chen Qi, Beuningen (NL); Hendricus Bartholomeus Andreas De Bont, Bennekom (NL); Luutsche Van Der Zee, Arnhem (NL); Mirian Lansink, Utrecht (NL); Klaske Van Norren, Renkum (NL)

(73) Assignee: N.V. Nutricia, MA Zoetermeer (NL)

( * ) Notice: Subject to any disclaimer, the term of this patent is extended or adjusted under 35 U.S.C. 154(b) by 543 days.

(21) Appl. No.: 09/726,308

(22) Filed: Dec. 1, 2000

(65) Prior Publication Data

US 2002/0068095 A1 Jun. 6, 2002

(51) Int. Cl.$^7$ .................. A61K 31/56; A61K 35/78; A61K 31/20; A61K 31/21; A61K 31/35
(52) U.S. Cl. .................. 514/171; 514/52; 514/78; 514/415; 514/458; 514/460; 514/510; 514/560; 514/783; 424/725; 424/728; 424/740; 424/746; 424/756; 424/764; 424/778; 424/779
(58) Field of Search .................. 424/725, 746, 424/756, 764, 728, 740, 778, 779; 514/171, 52, 78, 415, 458, 460, 510, 560, 783

(56) References Cited

U.S. PATENT DOCUMENTS 5,665,359 A    9/1997    Ho et al.

FOREIGN PATENT DOCUMENTS

| WO | 96/31132 | 10/1996 |
| WO | 98/57545 | 12/1998 |
| WO | 9911144 | * 3/1999 |
| WO | 00/30665 | 6/2000 |

OTHER PUBLICATIONS

Kevin B. Hicks et al., "Phytosterols and Phytostanols: Functional Food Cholesterol Busters," *Food Technology*, V. 55, 2001, pp. 63–67.

Vieno Piironen et al., "Plant Sterols: Biosynthesis, Biological Function and Their Importance to Human Nutrition," *J. Sci. Food Agric.*, V. 80, 2000, pp. 939–966.

* cited by examiner

Primary Examiner—Raymond J. Henley, III
Assistant Examiner—Leslie A. Royds
(74) Attorney, Agent, or Firm—Young & Thompson

(57) ABSTRACT

The invention provides a composition and a method for lowering blood serum cholesterol levels or for preventing elevated blood serum cholesterol levels, as well as suitable composition comprising (a) one or more phytosterols and/or phytostanols or a mixture thereof capable of reducing cholesterol absorption in the intestine, (b) a composition capable of inhibiting cholesterol biosynthesis, and (c) a composition capable of increasing cholesterol metabolism, wherein at least one of compositions b. and c. is preferably derived from plants.

23 Claims, No Drawings

CHOLESTEROL LOWERING SUPPLEMENT

BACKGROUND OF THE INVENTION

Cardiovascular diseases (CVD) are the major cause of death and disability in the United States and other industrialized countries despite recent declines in CVD mortality rates, They account for more deaths annually than any other disease, including all forms of cancer combined[i]. In the USA more than 1 million heart attacks occur each year and more than half a million people still die as a result. This enormous toll has focused attention on the possible prevention of CVD by various means, especially through lowering of plasma cholesterol levels. It is well established now that elevated total cholesterol, and in particular low-density lipoprotein (LDL) cholesterol, in plasma plays an important role in the development of atherosclerosis[ii]. Clinical trials have demonstrated clearly that decreasing cholesterol concentrations in plasma can contribute to primary and secondary prevention of coronary events and mortality.[iii] Some studies have estimated a 2% reduction in risk of a coronary artery event by a 1% reduction of total serum cholesterol.[iv]

[i] Levi, R. I., Declining Mortality in Coronary Heart Diseases, Artherosclerosis, 1981, 1, 312–325.
[ii] Cholesterol Adult Treatment Panel: Report of the National Cholesterol Education Program Expert Panel on Detection, Evaluation and Treatment of High Cholesterol in Adults, Arch. Intern. Med., 1988, 148,36–69.
[iii] Frick, M. H., et al., Primary prevention Trial with Gemfibrozil in Middle-aged Men with Dyslipidemia: Safety of Treatment, Changes in Risk Factors, and Incidence of Coronary Heart Disease. New Engl, J. Med, 1987, 317, 1237–1245. Pederson T. R. et al., Randomised Trial of Cholesterol Lowering in 4444 Patients with Coronary Heart Disease: The Scandinavian Simvastatin Survival Study (4S), The Lancet, 1994, 344, 1193–1389.
[iv] La Rosa, J. C, et al., The Cholesterol Facts: A Summary of the Evidence relating to Dietary Fats, Serum Cholesterol and Coronary Heart Disease: A Joint Statement by the American Heart Association and the National Heart, Lung and Blood Institute, Circulation, 1990, 81, 1721–1733. Law, M. R. et al, By how much and how quickly does Reduction in Serum Cholesterol Concentrations lower Risk of Ischemic Heart Disease? Br. Med. J., 1994, 308, 367–373.

Serum cholesterol levels can for example be lowered by a daily intake of some components similar to cholesterol. The components similar to cholesterol reduce the absorption of cholesterol from the intestines into the bloodstream.

U.S. Pat. No. 5,958,913 discloses a substance comprising a sawed sterol fatty acid ester capable of lowering LDL cholesterol levels in serum and which is fat soluble. The substance can be taken orally as a food additive, food substitute or supplement A daily consumption of saturated sterol fatty acid ester in an mount between about 0.2 and about 20 g/day has been shown to reduce the absorption of endogenic cholesterol.

Alternatively, compositions that inhibit the cholesterol biosynthesis, for example by inhibiting enzyme 3-hydroxy-3-methylglutaryl coenzyme A reductase (HMG-CoA reductase), an enzyme involved in the cholesterol biosynthesis, can lower blood serum cholesterol by slowing down the production of cholesterol. It is believed that inhibition of HIMG-CoA reductase results in a reduction in hepatic cholesterol synthesis and intracellular cholesterol stores, a compensatory increase in low-density lipoprotein (LDL) receptors, and a subsequent enhanced removal of LDL-cholesterol from plasma. Potent inhibitors of HMG-CoA reductase include for example the compounds referred to as statins, which family comprises for example lovastatin, pravastatin and fluvastatin.

Several studies suggested a HMG-CoA reductase iniibiting effect of plant extracts. Wang et al.[v] demonstrated HMG-CoA reductase inhibition by several aqueous plant extracts in isolated rat hepatic microsomal preparations. In vivo studies on rats demonstrated the inhibitory effect of traditional Chinese herbs on the cholesterol biosynthesis[vi].

[v] Wang, S. L. et al, Effects of Flos *Chrysanthemum* and several other Chinese herbs on in vitro HMGR activity of liver microsome of rast. Chinese J. of biochemistry, 1988, 4(6): 517–522.
[vi] Wang S. L. et al, Effects of Flos *Chrysanthemum* and other fourteen Chinese herbs on metabolism of cholesterol in rats. Chinese J. of biochemistry, 1987, 3(4):319–323.

An enzyme involved in the cholesterol metabolism (conversion of cholesterol into other components) is cholesterol 7α-hydroxylase. Hepatic cholesterol 7α-hydroxylase catalyses the conversion of cholesterol into 7α cholesterol, which is believed to be the rate limiting step in conversion of cholesterol into bile acids. It has been suggested that the increase of cholesterol 7α-hydroxylase activity results in the decrease of blood serum cholesterol and thus is an important pathway of elimination of cholesterol from the body. Methods for treatment of blood serum cholesterol related disorders by inhibition of cholesterol 7α hydroxylase are known in the art.

WO 91/15213 discloses a method for treatment of cholesterol gallstones employing side-chain hydroxylated cholesterol derivative. In particular the method for treatment of cholesterol gallstones involves ale administration of 25- or 26-hydroxycholesterol, which enhance the activity of cholesterol 7α-hydroxylase, thereby inhibiting for example cholesterol precipitation. Additionally, Wang et al.[vi] showed that several herbal preparations are capable of increasing cholesterol 7α hydroxylase activity.

According to Raicht et al.[vii], feeding cholesterol to rats increased cholesterol absorption from 1.2 to 70 mg/day and inhibited its synthesis in the liver and enhanced conversion of cholesterol to bile acids from 13.7 to 27.3 mg/day. Furthermore, when given cholesterol to the rats, HMG-CoA reductase activity was inhibited 80%. With beta-sitosterol, cholesterol absorption was inhibited but cholesterol synthesis was increased from 20.0 to 28.8 mg/day.

[vii] Raicht, R. F et al., Sterol balance studies in the rat. Effects of diet cholesterol and beta-sitosterol on sterol balance and ate-limiting enzymes of sterol metabolism. Biochimica et Biophysica Acta, 1975, 388(3): 374–384.

The majority of cholesterol lowering compositions currently known in the art include ingredients which either lower cholesterol absorption within the intestines or inhibit cholesterol biosynthesis, e.g., by inhibition of HMG-CoA reductase. As Raicht et al.[vii] demonstrated, the inhibition of cholesterol absorption in the intestine (using β-sitosterol) lowers cholesterol absorption, however, the inhibition of cholesterol absorption in the intestines is followed by an increase in HMG-CoA reductase activity. Increase of the HMG-CoA reductase activity is likely to increase cholesterol biosynthesis and thereby reduce the net effect of cholesterol absorption inhibitors. It is therefore desirable to decrease serum cholesterol levels using combination compositions, which reduce cholesterol absorption within the intestine and additionally inhibit cholesterol biosynthesis, e.g. by inhibiting HMG-CoA reductase activity, Methods of reducing plasma cholesterol levels comprising administering a combination of an effective amount of cholesterol biosynthesis inhibitor and an effective amount of cholesterol absorption inhibitor are disclosed in U.S. Pat. No. 5,661,145. The administered combination includes a beta-lactam cholesterol absorption inhibitor and a HMG-CoA reductase inhibitor, which can for example be a statin, for example lovastatin or pravastatin. Other pharmaceutical combination compositions including certain cholesterol absorption inhibitors and cholesterol synthesis inhibitors useful for the treatment of hypercholesterolemia and atherosclerosis are described in U.S. Pat. No. 5,807,834.

WO 98/01759 describes a method of determining in animal the ratio of serum campesterol to the level of β-sitosterol comprising several steps. Additionally, a combination composition for enhancing in an animal the inhibitory effect of phytostrols on cholesterol enterocyte absorption, which comprises one or more phytosterols which inhibit predominantly one or both of cholesterol and beta sitosterol and one or more compounds which limit cholesterol synthesis, e.g. compounds selected form HMG CoA reductase inhibitors, for example lovostatin, is described. Further described is the main disadvantage of the above composition i.e. the use of statins, and the critical side effects related with the use of statins.

WO 00/15201 discloses a composition for preventing and treating CVD containing phytosterols or phytostanols as agents inhibiting cholesterol absorption and tocotrienols as agents suppressing cholesterol biosynthesis.

WO 00/38725 provides combinations of cardiovascular therapeutic compounds for the prophylaxis or treatment of cardiovascular disease including hypercholesterolemia and atherosclerosis. Combinations disclosed include an ileal bile acid transport inhibitor combined with a cholesteryl ester transport protein inhibitor, a fibric acid derivative, a nicotinic acid derivative, a microsomal triglyceride transfer protein inhibitor, a cholesterol absorption antagonist, or others. Further combinations include a CETP inhibitor with a fibric acid derivative, a nicotinic acid derivative, a bile acid sequestrant, a microsomal triglyceride transfer protein inhibitor, a cholesterol absorption antagonist, or others.

U.S. Pat. No. 5,958,417 describes a herbal combination comprising Crataegus, Ho Shou Wu, *Cassia* Seed, *Chrysanthemum, Lotus* Leaf, *Alisma*, Hu-Zhang, and Rhubarb wherein the herbs are present in specific weight percentages. However, the herbal combination lacks a potent cholesterol absorption-inhibiting component, such as an effective amount of phytosterol and/or phytostanol.

Notwithstanding these disclosures, there remains a need in the art for compositions for use in reduction of blood serum cholesterol levels or prevention of elevated blood serum cholesterol levels. Combination compositions including cholesterol absorption inhibitors and cholesterol synthesis inhibitors useful for reduction of blood serum cholesterol levels known in the art are mostly chemically manufactured compositions and the known compositions are therefore undesirable for many people, not natural and costly.

Additionally, the combination compositions known in the art cannot be used frequently for a longer period since negative side effects will occur. Recent studies have indicated that drugs like statins, often used as HMG-CoA reductase inhibitors in combination compositions, and fibrates can be carcinogenic or cause other undesirable side effects. Newman et al[viii] reported that all members of the classes stains and fibrates cause cancer in rodents. Furthermore, two hyperlipidemic patients treated with simvastatin, a potent inhibitor of HMG-CoA reductase, experienced cheilitis after beginning treatment The rash resolved after discontinuation of medication and subsequent treatment with topical moisturizers and topical corticosteroids (Mebregan et al.[ix]). Khosla et al[x] alerts clinicians to the possible adverse effect of simvastati and other statins by reporting a case of a 79-year-old man who had onset of fatigue, myalgia, and pleuritic chest pain 3 months after initiation of therapy with simvastatin. Lovastatin was reported to cause liver failure (Tolman[xi]).

[viii] Newman et al., Carcinogenicity of lipid-lowering drugs. JAMA, 1996275(1): 55–60.
[ix] Mehregan D. R. et al., Cheilitis due to treatment with simvastatin. Cutis, 1998, 62(4):197–198.
[x] Koshla R. et al, Simvastatin-induced lupus erythematosus. South Med J., 1998, 91(9):873–874.
[xi] Tolman K. G., Defining patient risks from expanded preventive therapies. Am, J. Cardiol, 2000, 85(12A): 15E–9E.

Furthermore, combination compositions known in the art to date only comprise effective amounts of at most two of the blood serum cholesterol reducing activities, selected from reduction of cholesterol absorption in the intestine, inhibition cholesterol of biosynthesis and increase of cholesterol metabolism.

SUMMARY OF THE INVENTION

The invention disclosed here takes away the above problems and provides combination compositions for use in reduction of blood serum cholesterol levels or prevention of elevated blood serum cholesterol levels comprising one or more phytosterols and/or phytostanols or mixtures thereof capable of reducing cholesterol absorption in the intestine, an effective amount of a plant derived composition capable of inhibiting cholesterol biosynthesis and an effective amount of a plant derived composition capable of increasing cholesterol metabolism.

The combination composition disclosed here fulfills the need for cholesterol-reducing combinations having plant-derived active components. The composition according to the invention can therefore be administered for a longer period, thus making it suitable for use in compositions for reduction of blood serum cholesterol levels or prevention of elevated blood serum cholesterol levels. The invention provides a balanced composition for use in reducing blood serum cholesterol levels or preventing elevated blood cholesterol levels. These combination compositions avoid the potential side effects or compensator effects associated with the administration of relatively high levels of components solely directed at reducing cholesterol absorption in the intestine or at inhibiting cholesterol synthesis or at increasing cholesterol metabolism or at only two of those three mechanisms.

The present invention provides a composition for use in reduction of blood serum cholesterol levels or prevention of elevated blood serum cholesterol levels comprising:

a. one or more phytosterols and/or phytostanols or mixtures thereof capable of reducing cholesterol absorption in the intestine b. an effective mount of a composition capable of inhibiting cholesterol biosynthesis c. an effective amount of a composition capable of increasing cholesterol metabolism.

Advantageously, at least one of compositions b. and c. is derived from plants, i.e. obtained by extraction of plants, Preferably, both composition b. and composition c. are derived from plants, most preferably from different plants or different combinations of plants.

A further object of the present invention is to provide a method of reducing serum cholesterol levels or preventing elevated blood serum cholesterol levels comprising, administrating to a person a composition comprising one or more phytosterols and/or phytostanols or mixtures thereof capable of reducing cholesterol absorption in the intestine, an effective amount of a plant derived composition capable of inhibiting cholesterol biosynthesis and an effective amount of a plant derived composition capable of increasing cholesterol metabolism.

DESCRIPTION OF THE INVENTION

The term cholesterol biosynthesis is well known to those skilled in tie art and generally refers to the biochemical pathways of cholesterol synthesis within the animal (e.g. human) body. The term cholesterol metabolism is also well known to those skilled in the art and generally refers to the biochemical pathways involved in the removal of cholesterol from he body.

The phytosterol and/or phytostanol or mixtures thereof capable of reducing cholesterol absorption in the intestine can be any composition of phytosterol and/or phytostanol or mixtures thereof known in the art and having a cholesterol absorption reducing effect, Phytosterols are steroids derived from plants, yeasts or fungi, which have a hydroxyl group at C-3 and no other functional groups and differ from animal sterols, in particular cholesterol, in that the side chain at position 17 contains a double bond and/or an additional methyl, ethyl or ethylidene group, in particular at position 24. The term phytosterol and/or phytostanol according to the invention, comprises all such analogues, which may further have a double bond at the 5-position in the cyclic unit as in most natural phytosterols, or one or more double bonds at other positions (e.g. 6, 7, 8(9), 8(14), 14, 5/7, or no double bonds in the cyclic unit as in the stanols, or even additional methyl groups as e.g. in $\alpha_1$-sitosterol; the term includes natural phytosterols and derivatives thereof.

According to a preferred embodiment the phytosterol and/or phytostanols or us thereof are obtained from vegetable oil or wood pulp. More in particular, $\alpha$-, $\beta$-, $\gamma$-sitosterol, stigmasterol, ergosterol, campesterol, avenasterol, brassicasterol, desmosterol, chalinosterol, poriferasterol, clionasterol, sitostanol, stigmastanol, campestol or a mixture of one or more of the above phytosterols or phytostanols is used. According to an even more preferred embodiment, sitosterol or mixtures including a sitosterol are used, The concentration of phytosterols and/or phytostanols in composition a. is at least 10%, preferably at least 25%, more preferably at least 50%, most preferably at least 80% by dry weight of composition a.

The plant derived composition capable of inhibiting cholesterol biosynthesis according to the invention preferably comprises a composition capable of inhibiting the enzyme 3-hydroxy-3-methylglutaryl coenzyme A reductase (HMG-CoA reductase inhibitor) and/or inhibiting squalene synthase (squalene synthase inhibitor), HMG-CoA reductase inhibitors can decrease the activity of HMG-CoA reductase, thus inhibiting the conversion of HMG-CoA to mevalonate. The HMG-CoA reductase inhibitors can act on the HMG-CoA reductase directly or indirectly by decreasing the activity of one or more enzymes (e.g. HMG-CoA reductase phosphatse) or cofactors involved in the activation of HMG-CoA reductase or increasing the activity of one or more enzymes (e.g. HMG-CoA reductase kinase) or cofactors involved in the down regulation of HMG-CoA reductase or by decreasing the of HMG-CoA reductase gene transcription or of HMG-CoA reductase RNA translation.

Squalene synthase inhibitors can decrease the activity of squalene synthase, thus inhibiting the conversion of farnesyl pyrophosphate into squalene. Squalene synthase inhibitors can act on the squalene synthase directly, or indirectly by decreasing the activity of one or more enzymes or cofactors involved in the activation of squalene synthase; or increasing the activity of one or more enzymes or cofactors involved in the down regulation of squalene synthase; or decreasing the squalene synthase gene transcription or squalene synthase RNA translation. According to a preferred embodiment the composition capable of inhibiting cholesterol biosynthesis comprises one or more HMG-CoA reductase inhibitors.

The composition capable of inhibiting cholesterol biosynthesis is preferably obtained from whole plants or from one or more parts thereof, for example stems, stalks, roots, shoots, rhizomes, tubers, fruits, foliage, kernels, husks, hulls or mixtures thereof, Preferably, the composition is an extract from whole plants or plant parts. Such extracts can be obtained by harvesting the plants, optionally comminuting the plants and/or separating certain parts of the plants, drying, extracting the plants or plant parts using liquid extraction, and optionally concentrating the extract. Drying of the plants is usually necessary to avoid degradation of labile components or microbial contamination upon storage, transport or processing, and results in lowering the water content from e.g. 50–90% to e.g. less than 25%., preferably less than 20%, most preferably between 5 and 15%. Drying is performed under mild conditions i.e. at temperatures between 0 and 80° C., in particular between 10 and 60° C., or by freeze-drying. Before or after drying, the plants or plant parts may be reduced in particle size to coarse fragments or even to fine powder by processes such as grinding, flaking or mincing. Grinding using a hammer mill or equivalent machine is preferred. Extraction according to the invention refers to separating the desired plant material by physical or chemical means, preferably with the aid of a solvent. Suitable solvents include water, water-alcohol mixtures, alcohols, ethers, hydrocarbons or other organic solvents or mixtures thereof Water and water-based solvent mixtures are preferred. Extraction can be performed by maceration, i.e. soaking for a time between e.g. one minute and several hours, optionally using agitation, followed by filtration. For larger scale operations, counter-current extraction can be used. The resulting solutions can be concentrated to liquid or solid extracts using e.g. tin layer evaporators, freeze-drying or spray-drying techniques. Spray-drying resulting in concentrated to dry powders is preferred. Suitable plant extracts containing inhibitors of cholesterol biosynthesis are commercially available.

Preferred sources for the composition capable of inhibiting cholesterol biosynthesis include *Alisma orientale* (pharmaceutical name Rhizoma alismatis);*Typha* spp., for example *Typha angustifolia* or *Typha orientalis* (pharmaceutical name Pollen Typhea); *Salvia miltiorhiza* (pharmaceutical name Radix salviae mniltiorrhizae); *Polygonum mulliflorum* (pharmaceutical name Radix Polygoni multiflora);*Curcuma* spp., for example *C. kwangsiensis, C. longa, C. phaecaulis, C. wenyuin* or *C. aromatica*, (pharmaceutical name Radix curcmae or Rhizoma curcumae); *Ligusticum* spp., for example *L. wallichii*, (pharmaceutical name Rhizoma Ligustici); *Polygonatum* spp., for example *P. kingianum, P. sibiricum* or *P. cyrtonema* (pharmaceutical name Rhizoma polygonati); *Polygonum cuspidatum* (pharmaceutical name Rhizoma polygoni cuspidati); *Corydalis* spp, (pharmaceutical name Rhizoma Corydalis); *Chrysanthemum morifolium* (pharmaceutical name Flos Chrysathemi); *Arthemisia capillaris* (pharmaceutical name Herba Arimisiae capillaris); *Crataegus pinnatifida* or its variations or subspecies pharmaceutical name Fructus Crataegi pinnatifidae); *Eleutheroccus senticocus* (pharmaceutical name Radix eleutherococci senticosi); *Astragalus membranaceus* (pharmaceutical name Radix Astragali). According to a particularly preferred embodiment *Polygonum multiflorum* is used as a source for tile composition capable of inhibiting cholesterol biosynthesis, more preferably at aqueous extract of *Polygonum multiflorum*.

Preferably, the composition capable of increasing cholesterol metabolism increases the conversion of cholesterol into bile acids and/or inhibits the esterification of cholesterol. According to an even more preferred embodiment, the composition capable of increasing cholesterol metabolism enhances the activity of cholesterol 7α-hydroxylase (cholesterol-7α hydroxylase activator) and/or inhibits the activity of Acyl-CoA acyl transferase (Acyl-CoA acyl transferase inhibitor).

A cholesterol 7α-hydroxylase activator can enhance the activity of cholesterol 7α-hydroxylase, thus enhance the conversion of cholesterol into 7α-cholesterol. Cholesterol 7α-hydroxylase activators can act on the cholesterol 7α-hydroxylase directly or indirectly by increasing the activity of enzymes and cofactors involved in the activation of cholesterol 7α-hydroxylase or decrease the activity of enzymes or cofactors involved in the down-regulation of cholesterol 7α-hydroxylase (e.g. by effecting enzymes involved in the phosphorylation and dephosphorylation of cholesterol 7α-hydroxylase) or increasing the cholesterol 7α-hydroxylase gene transcription or cholesterol 7α hydroxylase RNA translation.

Acyl-CoA acyl transferase inhibitors can inhibit the conversion of cholesterol into cholesteryl oleate. Acyl-CoA acyl transferase inhibitors can act on tile Acyl-CoA acyl transferase directly, or indirectly by decreasing the activity of one or more enzymes or cofictors involved in the activation of Acyl-CoA acyl transferase or increasing the activity of one or more enzymes or cofactors involved in the down regulation of Acyl-CoA acyl transferase or decreasing the Acyl-CoA acyl transferase gene transcription or Acyl-CoA acyl tslerase RNA translation. According to a preferred embodiment, the composition capable of increasing cholesterol metabolism comprises one or more cholesterol 7a-hydroxylase activators, which act systemically.

The composition capable of enhancing cholesterol metabolism is preferably obtained from whole plants or from one or more parts thereof, for example stems, stalks, roots, shoots, rhizomes, tubers, fruits, foliage, kernels, husks, hulls or mixtures thereof. The whole plants or plant parts providing enhancers of cholesterol metabolism may be subjected to extraction as described above for plants providing inhibitors of cholesterol biosynthesis, Suitable extracts containing the plant-derived metabolic enhancers are commercially available.

Preferred sources for obtaining the compositions capable of increasing cholesterol metabolism include *Polygonum multiflorum* (pharmaceutical name Radix Polygoni multiflora); *Curcuma* spp., for example *C. kwangsiensis, C. longa, C. phaecaulis, C. wenyuin* or *C. aromatica*, pharmaceutical name Radix curcumae or Rhizoma curcutmae); *Ligusticum* spp., for example *L. wallichii*, (pharmaceutical name Rhizoma Ligustici); *Polygonatum* spp., for example *P. kingianum, P. sibiricum* or *P. cyrtonema* (pharmaceutical name Rhizoma polygonati); *Polygonum cuspidatum* (pharmaceutical name Rhizoma polygoni cuspidati); *Corydalis* spp. (pharmaceutical name Rhizoma Corydalis); *Chrysanthemum morifolium* (pharmaceutical name Flos Chrysanthemi); *Arthemisia capillaris* (pharmaceutical name Herba Artimisiae capillaris); *Acanthopanax senticosus* (pharmaceutical name Radix Astragali). According to a particularly preferred embodiment *Chrysanthemum morfolium* is used as a source for the composition capable of increasing cholesterol metabolism, more preferably an aqueous extract *Chrysanthemum morifolium*.

The dry weight ratio between composition a. and the combination of compositions b. and c. is preferably between 0:1 and 1:10, more preferably between 4:1 and 1:4. The dry weight ratio between compositions b. and c, is preferably between 10:1 and 1:10, more preferably between 3:1 and 1:3.

Elevated serum cholesterol levels are often closely related to a reduced vascular health. It is therefore advantageously to include in the composition for use in reduction of blood serum cholesterol levels or prevention of elevated blood serum cholesterol levels, an effective amount of a composition for the prevention and/or treatment of vascular disorders. Preferably one or more compounds selected from the group of polyunsaturated fatty acids, antioxidants, phospholipids, folic acid, vitamin B12, vitamin B6, magnesium, coenzyme Q10 and zinc are included in the composition according to the invention. These compositions may serve as additives or potentiators, thus increasing the cholesterol lowing effect of phytosterols and/or phytostanols, and/or for teament and prevention of vascular disorders. Preferred polyunsaturated fatty acids are omega-6-fatty acids or omega-3-fatty acids or mixtures thereof, for example eicosapentaenoic acid, docosahexaenoic acid or linoleic acid. As a preferred antioxidant, a tocopherol, for example vitamin E, is used. As a preferred phospholipid, lecithin is used.

According to an even further preferred embodiment, long chain polyunsaturated fatty acids, phospholipids and a compound selected from the group of folic acid, vitamin B12, vitamin B6, magnesium, zinc are included in composition for use in reduction of blood serum cholesterol levels or prevention of elevated blood serum cholesterol levels.

The composition according to the invention is preferably administered orally. The composition can for example be added to food or feed products such as beverages or products with a substantial oil content or ingested as nutritional supplement in the form of for example tablet, capsule, microbead, emulsion, powder, granule, suspension, syrup, elixir, chewing gums and the like.

Preferred daily intake amounts of the components according to the invention greatly depend on the concentration of available and/or active component present in the composition. This is especially applicable for the plant-derived material capable of inhibiting cholesterol biosynthesis and the composition capable of increasing cholesterol metabolism, According to a preferred embodiment, the daily dose of the composition according to the invention includes about 0.01 to 5 gram phytosterol and/or phytostanol or mixtures thereof, more preferably about 0.1 to 1 gram, most preferred about 0.2 to 0.6 gram. The composition capable of inhibiting cholesterol biosynthesis preferably comprises per daily dose about 0.01 to about 30 gram, depending on the type of herbal preparation used. For example, when using crude preparations of *Polygonum multiflorum*, e.g. unprocessed root, the daily intake is preferably between about 0.5 gram and about 15 gram. When processed *Polygonum multiflorum* is used (the process for preparation of processed *Polygonum multiflorum* is well known in the art and reduces LD50 value of *Polygonum multiflorum* compared to crude *Polygonm multiflorum*), the daily intake is preferably between about 0.5 gram and about 30 gram. According to a preferred embodiment of this invention, concentrated extracts of one or more of the plant sources are used. According to a further preferred embodiment, a concentrated extract of *Polygonumn mutiflorum* is used, corresponding to about 0.5 to out 30 gram crude *Polygonum multiflorum*, preferably about 3–10 gram crude *Polygonum muliflorum*. Thus when using an aqueous extract having an concentration ratio of 16:1 (16 times concentrated), the daily intake is preferably about 0,05 gram to about 2 grams, even more preferably about 0.1 gram to about 0.7 gram of the extract.

The composition capable of increasing cholesterol metabolism preferably comprises per daily dose about 0.01 to about 30 gram depending on the type of herbal preparation used. For example, when using crude preparations of *Chrysanthemum morifolium*, e.g. unprocessed flower, the daily intake is preferably about 1 gram to about 15 gram. According to a preferred embodiment, a concentrated extract of *Chrysanthemum morifolium* is used corresponding to about 1–15 grain crude *Chrysanthemum morifolium*, preferably about 3–10 gram crude *Chrysanthemum morifolium*. Thus when using an aqueous extract of *Chrysanthemum morifolium* having an concentration ratio of about 10:1 (10 times concentrated), the daily intake is preferably about 0.01 gram to about 3 grams, even more preferably about 0.1 gram to about 0.7 gram of the extract.

EXAMPLE 1

Capsule Composition I

A capsule comprising:
500 mg phytosterol mixture; including about brassicasterol (6%), campesterol (30%), stigmasterol (22%), sitosterol (58%).
250 mg concentrated Radix Polygoni multiflora water extract with concentration ratio of 16:1 (obtainable form P.L. Thomas & Co, Inc, having address Morristown, N.J. 07980)
200 mg Flos Chrysanthemi extract (obtainable form MTC Nutricions, Inc, Whitestone, N.Y. 11357)

EXAMPLE 2

Capsule Composition II

A capsule comprising:
500 mg phytosterol mixture; including about brassicasterol (6%), campesterol (30%), stigmasterol (22%), sitosterol (580%).
250 mg Radix Polygoni multiflora extract
200 mg Flos Chrysanthlemi extract
400 mg lecithin
60 mg eicosapentaenoic acid
60 mg docosahexaenoic acid

EXAMPLE 3

Capsule Composition III

The capsule described in example 1, further comprising:
1000 mg soybean oil
150 mg lauric acid and monoolein.

EXAMPLE 4

Capsule Composition IV

The capsule described in example 2, further comprising:
400 IU vitamin B.

What is claimed is:
1. A composition comprising:
   a. one or more phytosterols and/or phytostanols or a mixture thereof capable of reducing cholesterol absorption in the intestine;
   b. a composition capable of inhibiting cholesterol biosynthesis;
   c. a composition capable of increasing cholesterol metabolism,
   wherein at least one of compositions b. and c. is derived from plants.
2. A composition according to claim 1, wherein the at least one of compositions b. and c. is an extract from a plant or plant parts.
3. A composition according to claim 2, wherein compositions b. and c. are extracts from different plants or parts thereof.
4. A composition according to claim 1, wherein composition b. capable of inhibiting cholesterol biosynthesis comprises one or more HMG-CoA reductase inhibitors and/or squalene synthase inhibitors.
5. A composition according to claim 4, wherein the composition capable of inhibiting cholesterol biosynthesis comprises one or more NMG-CoA reductase inhibitors.
6. A composition according to claim 4, wherein the composition capable of inhibiting cholesterol biosynthesis is derived from a plant or plant part selected from the group consisting of *Alisma orientale, Typha* spp., *Salvia miltiorhiza, Polygonum multiflorum, Curcuma* spp., *Ligusticum* spp., *Polygonun* spp., *Polygonun cuspidatum; Corydalis* spp; *Chrysanthemum morifolium; Arthemisia capillaris; Crataegus pinnatifida, Eleutheroccus senticocus, Astragalus membranaceus* and subspecies or varieties thereof.
7. A composition according to claim 6, wherein the composition capable of inhibiting cholesterol biosynthesis is an aqueous extract of *Polygonum multiflorum*.
8. A composition according to claim 1, wherein composition a. contains at least 25% by weight of phytosterols and/or phytostanols.
9. A composition according to claim 1, wherein the phytosterol and/or phytostanol or mixture thereof comprises a plant sterol obtained from vegetable oil or wood pulp.
10. A composition according to claim 9, comprising a phytosterol selected from the group consisting of sitosterol, stigmasterol, ergosterol, campesterol, avenasterol, brassicasterol, desmosterol, chalinosterol, poriferasterol, clionasterol, sitostanol, stigmastanol and campestanol.
11. A composition according to claim 1, wherein composition c. capable of increasing cholesterol metabolism comprises an effective amount of a composition capable of increasing conversion of cholesterol into bile acids and/or inhibiting the esterification of cholesterol.
12. A composition according to claim 11, wherein composition c. comprises one or more cholesterol 7a-hydroxylase activators and/or one or more Acyl-CoA acyl transferase inhibitors.
13. A composition according to claim 12, wherein the composition capable of increasing cholesterol metabolism is derived from a plant or plant part selected from the group consisting of *Polygonum multiflorum, Polygonum cuspidatum, Curcuma* spp., *Ligusticum* spp., *Polygonatum* spp., *Corydalis* spp., *Chrysanthemum morifolium, Arthemisia capillaris* and *Acanthopanax senticosus*.
14. A composition according to claim 13, wherein the composition comprising an effective amount of a composition capable of increasing cholesterol metabolism is an aqueous extract of *Chrysanthemum morifolium*.
15. A food or beverage product comprising a composition according to claim 1.
16. A nutritional supplement comprising a composition according to claim 1.
17. A tablet, capsule, microbead, emulsion, powder, granule, suspension, syrup, elixir or chewing gum comprising a composition according to claim 1.
18. A composition according to claim 1, further comprising a component selected from the group consisting of poly-unsaturated fatty acids, antioxidants, phospholipids, folic acid, vitamin B12, vitamin B6, magnesium, coenzyme Q10 and zinc.
19. A composition according to claim 18, wherein the polyunsaturated fatty acids comprise omega-6-fatty acids and/or omega-3-fatty acids.

20. A composition according to claim 18, wherein the phospholipids comprise lecithin.

21. A composition according to claim 18, wherein the antioxidants comprise tocopherols.

22. A composition according to claim 21, wherein the tocopherols comprise vitamin E.

23. A method of reducing serum cholesterol levels or inhibiting elevated blood serum cholesterol levels comprising administering to a person in need thereof an effective amount of a composition comprising:

a. one or more phytosterols and/or phytostanols or a mixture thereof capable of reducing cholesterol absorption in the intestine;

b. a plant-derived composition capable of inhibiting cholesterol biosynthesis; and c. a plant-derived composition capable of increasing cholesterol metabolism.

* * * * *